(12) United States Patent
Knauf et al.

(10) Patent No.: US 10,125,091 B2
(45) Date of Patent: *Nov. 13, 2018

(54) PROCESS FOR PREPARATION OF DI- AND POLYAMINES OF THE DIPHENYLMETHANE SERIES

(71) Applicant: Covestro Deutschland AG, Leverkusen (DE)

(72) Inventors: Thomas Knauf, Dormagen (DE); Stefan Wershofen, Monchengladbach (DE); Klaus-Gerd Gruner, Duisburg (DE); Volker Hartjes, Duisburg (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/318,102

(22) PCT Filed: Jun. 22, 2015

(86) PCT No.: PCT/EP2015/063923
§ 371 (c)(1),
(2) Date: Dec. 12, 2016

(87) PCT Pub. No.: WO2015/197520
PCT Pub. Date: Dec. 30, 2015

(65) Prior Publication Data
US 2017/0107171 A1    Apr. 20, 2017

(30) Foreign Application Priority Data

Jun. 24, 2014 (EP) .................................... 14173582

(51) Int. Cl.
*C07C 209/78* (2006.01)

(52) U.S. Cl.
CPC .................................. *C07C 209/78* (2013.01)

(58) Field of Classification Search
None
See application file for complete search history.

(56) References Cited

U.S. PATENT DOCUMENTS

| 4,792,624 A | 12/1988 | Hatfield, Jr. et al. |
| 5,053,539 A | 10/1991 | Yano et al. |

(Continued)

FOREIGN PATENT DOCUMENTS

| DE | 844896 | 9/1952 |
| GB | 1517585 | 7/1978 |

OTHER PUBLICATIONS

Treybal, Robert E.; Mass-Transfer Operations; Third Edition; 1980; McGraw-Hill Book Co.; pp. 477-541.

(Continued)

*Primary Examiner* — Clinton A Brooks
(74) *Attorney, Agent, or Firm* — Donald R. Palladino

(57) ABSTRACT

The invention relates to a method for the preparation of di- and polyamines of the diphenylmethane series (MDA) from aniline and formaldehyde, care being taken during the start up that a sufficient excess of aniline with respect to formaldehyde is ensured, said excess amounting to at least 105% of the desired molar ratio of aniline to formaldehyde for the target recipe of the MDA to be produced.

12 Claims, 1 Drawing Sheet

(56) References Cited

U.S. PATENT DOCUMENTS

| | | | |
|---|---|---|---|
| 5,208,368 A | * | 5/1993 | Scherzer ............ C08G 18/7664 |
| | | | 560/333 |
| 5,286,760 A | | 2/1994 | Bolton et al. |
| 6,433,219 B1 | | 8/2002 | Ströfer et al. |
| 6,576,788 B1 | | 6/2003 | Penzel et al. |
| 6,649,798 B2 | | 11/2003 | Klein et al. |
| 6,831,192 B2 | | 12/2004 | Ströfer et al. |
| 7,186,857 B2 | | 3/2007 | Müller et al. |
| 7,230,130 B2 | | 6/2007 | Ströfer et al. |
| 7,253,321 B2 | | 8/2007 | Hagen et al. |
| 7,312,362 B2 | | 12/2007 | Keggenhoff et al. |
| 7,528,283 B2 | | 5/2009 | Pohl et al. |
| 9,138,717 B2 | | 9/2015 | Ding et al. |
| 2009/0240077 A1 | | 9/2009 | Wershofen et al. |
| 2017/0114000 A1 | * | 4/2017 | Knauf .................. C07C 209/78 |

OTHER PUBLICATIONS

Twitchett, H. J.; Chemical Society reviews; 1974; 3(2); "Chemistry of the Production of Organic Isocyanates"; pp. 209-230.
Kirk-Othmer Encyclopedia of Chemical Technology (see "http://onlinelibrary.wiley.com/book/10.1002/0471238967"); John Wiley & Sons, Inc.; Extraction, Liquid-Liquid; pp. 22-23 (mixer-settler cascades or settling vessels); published online: Jun. 15, 2007.
Müller, E. et al; Ullmann's Encyclopedia of Industrial Chemistry; "Liquid-Liquid Extraction"; vol. 21; pp. 272-274; 2012 Wiley VCH Verlag GmbH & Co. KGaA, Weinheim, DOI: 10.1002/14356007.b03_06.pub2.

* cited by examiner

PROCESS FOR PREPARATION OF DI- AND POLYAMINES OF THE DIPHENYLMETHANE SERIES

CROSS-REFERENCE TO RELATED APPLICATIONS

This application is a national stage application of under 35 U.S.C. § 371 PCT/EP2015/063923, filed Jun. 22, 2015, which claims the benefit of European Application No. 14173582.9, filed Jun. 24, 2014, both of which being incorporated by reference herein.

FIELD

The invention relates to a process for preparing diamines and polyamines of the diphenylmethane series (MDA) from aniline and formaldehyde, in which care is taken during the start-up procedure to ensure that there is a sufficient excess of aniline over formaldehyde which is at least 105% of the molar ratio of aniline to formaldehyde wanted for the target formulation of the MDA to be produced.

BACKGROUND

The continuous or partially discontinuous preparation of MDA is disclosed, for example, in EP 1 616 890 A1, U.S. Pat. No. 5,286,760, EP-A-451442 and WO-A-99/40059. The acidic condensation of aromatic amines and formaldehyde to form diamines and polyamines of the diphenylmethane series proceeds in a plurality of reaction steps.

In the aminal process, formaldehyde is firstly condensed with aniline in the absence of an acid catalyst to form aminal, with water being eliminated. The rearrangement to form MDA is then carried out in the presence of an acid catalyst in a first step to form para- and ortho-aminobenzylaniline. The aminobenzylanilines rearrange in a second step to form MDA. Main products of the acid-catalyzed reaction of aniline and formaldehyde are the diamine 4,4'-MDA, its positional isomers 2,4'-MDA and 2,2'-MDA and also higher homologs.

In the neutralization process, aniline and formaldehyde are converted directly in the presence of an acid catalyst into aminobenzylanilines which subsequently react further to form the two-ring MDA isomers and MDA homologs having more than two rings. Regardless of the process variant for preparing the acidic reaction mixture, the work-up thereof is commenced according to the prior art by neutralization by means of a base. The neutralization is usually carried out at temperatures of, for example, from 90° C. to 100° C. without addition of further substances. (H. J. Twitchett, Chem. Soc. Rev. 3(2), 223 (1974)). However, it can also be carried out at a different temperature level, for example in order to accelerate the degradation of interfering by-products. Hydroxides of the alkali and alkaline earth elements are suitable as bases. Preference is given to using aqueous NaOH.

After the neutralization, the organic phase is separated from the aqueous phase in a separation vessel. The organic phase containing crude MDA which remains after the aqueous phase has been separated off is subjected to further work-up steps, for example washing with water (base wash) in order to wash residual salts out of the crude MDA. The crude MDA which has been purified in this way is subsequently freed of excess aniline, water and other materials present in the mixture (e.g. further solvents) by suitable methods such as distillation, extraction or crystallization.

The work-up customary in the prior art is disclosed, for example, in EP 1 652 835 A1, page 3, line 58 to page 4, line 13, or EP 2 103 595 A1, page 7, lines 21 to 37.

EP 2 486 975 A1 discloses the use of a specific mixer-reactor in the preparation of MDA. It is stated that a local excess of formaldehyde can lead to formation of network-like polymers. However, the patent application gives no details regarding the configuration of the start-up of the reaction, i.e. the commencement or resumption of the process after any interruption. In particular, the patent application does not teach that the "A/F ratio" (the molar ratio of aniline to formaldehyde) during the start-up procedure should be above the A/F ratio during normal operation.

EP 1 616 890 A1 teaches that aniline and formaldehyde are firstly reacted in the absence of the acid catalyst to form aminal and the aminal is subsequently admixed with the acid catalyst and is reacted further at temperatures of from 20° C. to 100° C. and at water contents of the acidic reaction mixture obtained in this way of from 0 to 20 percent by weight. In particular, the water is firstly at least partly removed from the aminal after the condensation of formaldehyde and aniline to form the aminal, with a water content of from 0 to 5 percent by weight in the aminal being set, and the aminal is subsequently admixed with an acid catalyst and is reacted further at temperatures of from 20° C. to 100° C. and at water contents of the acidic reaction mixture obtained in this way of from 0 to 20 percent by weight. Thus in this way, mixtures of diamines and polyamines of the diphenylmethane series having degrees of protonation of <15%, preferably from 4% to 14%, particularly preferably from 5% to 13%, can be prepared. Here, the degree of protonation is in the case of monoprotic acid catalysts (such as hydrochloric acid) the molar ratio of the amount of acid catalyst used and the molar amount of amine functions present in the reaction mixture.

The patent application gives no details regarding the procedure during the start-up procedure of an industrial production plant. The examples given are laboratory experiments. In particular, this patent application does not teach that the A/F ratio during the start-up procedure should be above the A/F ratio during normal operation.

EP 0 283 757 A1 is likewise concerned with the preparation of MDA. The process described is characterized by the addition of aniline-free MDAs to aminobenzylamines formed by condensation of aniline and formaldehyde before the heat-induced rearrangement reaction of the latter. Example 2 describes a mode of operation in which a small part of the MDA formed is recirculated to the rearrangement reaction (cf. also claims 6 and 8). In other words: the configuration of an MDA plant in continuous normal operation is described. Details regarding the procedure during start-up of an MDA plant are not described; in particular, there is no information regarding the A/F ratio during start-up compared to the A/F ratio during the reaction.

WO-A-99/40059 teaches that, to prepare methylenedi(phenylamine) by reaction of aniline with formaldehyde in the presence of acid catalysts in a semicontinuous process, aniline and optionally acid catalyst are initially charged, formaldehyde and optionally acid catalyst is fed through a mixing device into a circuit in which aniline, optionally acid catalyst and optionally previously added formaldehyde are circulated and, after introduction of at least 50% of the total amount of formaldehyde to be fed in, the reaction mixture is brought to a temperature of greater than 75° C. The addition up to an amount of at least 50% of the total amount of formaldehyde to be fed in is carried out at a temperature of the reaction mixture in the circuit of from 20° C. to 75° C.

None of the abovementioned documents of the prior art suggests using an A/F ratio which deviates from that during normal operation during start-up of the reaction for preparing MDA. Thus, it is quite customary in the prior art to use A/F ratios which are above that prescribed by the stoichiometry of the reaction (2:1) during normal operation. However, the prior art does not in any way suggest maintaining even greater A/F ratios during start-up.

The quality of a process for preparing MDA is defined firstly by the content of undesirable by-products of the reaction in the product. Secondly, the quality of a process is defined by the total process from start-up, normal production to running-down of the process to be able to be operated without technical production failure or problems which require intervention in the process and by losses of starting materials, intermediates or end product not occurring.

Such problems can, for example, occur during start-up of the aminal reaction. Such problems can be, for example, the formation of high molecular weight solids which lead to caking and blockages on the equipment (aminal vessel, cooler and separator and conduits).

Although it is possible to prepare MDA in high yield in the described processes of the prior art without the quality of the end products suffering, only processes which are in normal operation are described. Start-up processes up to attainment of a stable operating state at the desired load (known as "start-up time") are not taken into account. A semicontinuously or continuously operated industrial process cannot, proceeding from a production plant which is not in operation (e.g. after a stoppage for maintenance purposes), be brought back to the process parameters before the production stoppage in an instant. Starting materials and apparatuses have to be heated up, apparatuses may have to be made inert, the supply of starting material to the apparatuses is gradually increased to the desired value. Start-up and running-down times occur frequently on an everyday basis in industrial processes and are not necessarily associated with opening or other mechanical intervention in a reactor or another apparatus of the plant, but can also be connected with the shutting down and restarting of the production plant for various other reasons, e.g. lack of raw material. These start-up times are characterized in practice by deviations in the desired molar ratio of aniline to formalin being able to occur.

SUMMARY

It would therefore be desirable to have an improved process for preparing diamines and polyamines of the diphenylmethane series, with the focus being placed on the period of time during which the aminal reaction is started up. It is an object of the present invention to provide such a process.

This object is achieved according to the invention by a process for preparing diamines and polyamines of the diphenylmethane series (MDA) by reaction of aniline (1) and formaldehyde (2) at a desired molar ratio of aniline (1) to formaldehyde (2) of $A/F_{target}$, which preferably has a value of from 1.5 to 20, particularly preferably from 1.5 to 15, very particularly preferably from 1.5 to 10 and very especially preferably from 1.5 to 6, which comprises the steps:

Either, according to a variant A)

A.I) reaction of aniline (1) and formaldehyde (2) in the absence of an acid catalyst (3) in a reactor to form an aminal, with aniline (1) and formaldehyde (2) being introduced into the reactor, and subsequent separation of the reaction mixture obtained into an aqueous phase and an organic, aminal-containing phase;

A.II) reaction of at least part of the organic, aminal-containing phase obtained in step A.I) with acid (3) in a reactor, with the aminal reacting to form diamines and polyamines of the diphenylmethane series;

wherein the following steps are carried out for start-up of the process and/or resumption of the process after an interruption of at least the step A.I):

A.I.1) introduction of aniline (1) into the reactor of step A.I) at a mass flow rate $m_1$ commencing at the point in time $t_0$;

A.I.2) introduction of formaldehyde (2) into the reactor of step A.I), commencing at a point in time $t_1$, starting from a mass flow rate $m_2=0$ at the point in time $t_1$ to a mass flow rate $m_2=m_{2,intended}$ at the point in time $t_2$, where $t_2>t_1>t_0$;

A.II.1) in the case of interruption of the step A.II) too, introduction of acid (3) into the reactor of step A.II) at the latest when, as soon as or after, preferably as soon as or after, particularly preferably after, organic, aminal-containing phase is introduced for the first time into the reactor of step A.II);

where the introduction of aniline (1) in step A.I.1) and the introduction of formaldehyde (2) in step A.I.2) occur in such a way that the instantaneous molar ratio of the total aniline (1) introduced into the reactor of step A.I)

to the total formaldehyde (2) introduced into the reactor of step A.I), $A/F_{inst}$ is always ≥2 and ≥1.05·$A/F_{target}$ during the period of time from $t_1$ to $t_2$;

or, according to a variant B),

B.I) reaction of aniline (1) and acid (3) in a reactor to form a reaction mixture containing the anilinium salt of the acid (3) used;

B.II) reaction of at least part of the reaction mixture obtained in step B.I) with formaldehyde (2) in a reactor, forming diamines and polyamines of the diphenylmethane series;

wherein the following steps are carried out for the start-up of the process and/or the resumption of the process after an interruption of the steps B.I) and B.II):

B.I.1) introduction of aniline (1) into the reactor of step B.I) at an aniline mass flow rate $m_1$ commencing at the point in time $t_0$;

B.I.2) introduction of acid (3) before, simultaneously with or after introduction of aniline (1);

B.II.1) introduction of formaldehyde (2) into the reactor of step B.II), optionally together with further aniline (1), optionally together with further acid (3), commencing at a point in time $t_1$, proceeding from a mass flow rate $m_2=0$ at the point in time $t_1$ to a mass flow rate $m_2=m_{2,intended}$ at the point in time $t_2$, where $t_2>t_1>t_0$;

where the introduction of aniline (1) in step B.I.1) and optionally in step B.II.1) and the introduction of formaldehyde (2) in step B.II.1) occur in such a way that the instantaneous molar ratio of the total aniline (1) introduced into the reactor of step B.I) and, if present, the total aniline (1) introduced into the reactor of step B.II)

to the total formaldehyde (2) introduced into the reactor of step B.II), $A/F_{inst}$ is always ≥2 and ≥1.05·$A/F_{target}$ during the period of time from $t_1$ to $t_2$.

DETAILED DESCRIPTION

Figure 1:
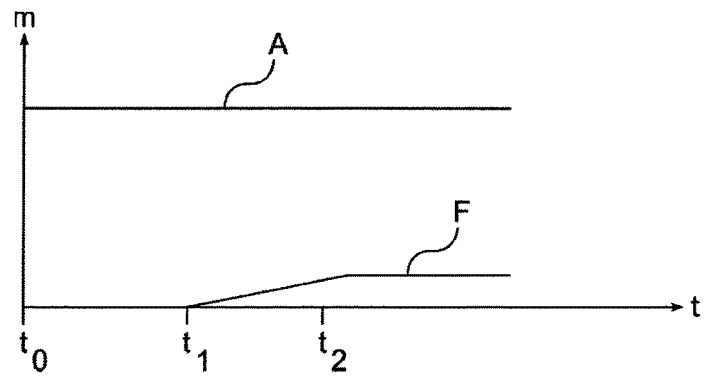
FIGS. 1 and 2 show the course over time of the mass flow ratio of aniline and formaldehyde in embodiments of the process of the invention.

For the purposes of the present invention, "diamines and polyamines of the diphenylmethane series" are amines and mixtures of amines of the following type:

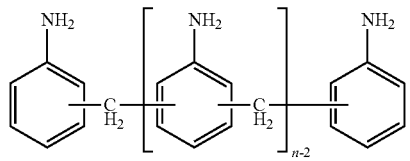

Here, n is a natural number of >2. In the following, the compounds of this type in which n=2 will also be referred to as diamines of the diphenylmethane series or diaminodiphenylmethanes (hereinafter MMDA). Compounds of this type in which n is >2 will for the purposes of the present invention also be referred to as polyamines of the diphenylmethane series or polyphenylenepolymethylenepolyamines (hereinafter PMDA). Mixtures of the two types will also be referred to as diamines and polyamines of the diphenylmethane series (hereinafter MDA). Industrially, the diamine and polyamine mixtures are predominantly converted into the corresponding diisocyanates and polyisocyanates of the diphenylmethane series by phosgenation.

In both variants, the reactors of steps I) and II) can be identical or different. This means that in variant A) it is possible either for the aminal formed in step A.I) to be left in the reactor and the acid to be added or for the aminal to be transferred to another reactor and the acid (3) then to be added there. In variant B), it is possible either for the reaction product formed from aniline (1) and acid (3) in step B.I) to be left in the reactor and the formaldehyde (2) to be added or for the reaction product of aniline (1) and acid (3) to be transferred to another reactor and the formaldehyde (2) then to be added there. Furthermore, the term "a reactor" also encompasses, for the purposes of the present invention, the case of a reactor cascade being used (in other words, the word "a" is in this context to be interpreted as the indefinite article and not as an indication of number).

In both variants, the steps I) and II) are carried out continuously or semicontinuously, preferably continuously.

The formaldehyde mass flow rate $m_{2,intended}$ is the formaldehyde mass flow rate $m_2$ at the desired production capacity (the desired load, "intended load"). The intended molar ratio of aniline (1) to formaldehyde (2), $A/F_{target}$, i.e. the molar ratio of aniline to formaldehyde ($CH_2O$) in the target formulation, determines the size of the feed streams (1) and (2) at the intended load ($A/F_{target}=[M_{1,intended}/M_1]/[M_{2,intended}/M_2]$, where $M_1$=molar mass of aniline and $M_2$=molar mass of formaldehyde, $CH_2O$). Thus, the $A/F_{target}$ ratio relates to the period of time after conclusion of start-up of production.

The instantaneous molar ratio, $A/F_{inst}$, in the period of time from $t_1$ to $t_2$ can be derived in the case of variant A) in a simple manner from the known feed streams (1) and (2) into the reactor of step A.I). at a particular point in time t taking into account the known amount of aniline (1) which has already been introduced into the reactor of step A.I). up to the point in time $t_1$. In the case of variant B), the instantaneous molar ratio, $A/F_{inst}$, in the period of time from $t_1$ to $t_2$ can be derived in an analogous way from the known feed streams (1) and (2) into the reactor of step B.I) or into the reactor of step B.II) at a particular point in time t taking into account the known amount of aniline (1) which has been introduced into the reactor of step B.I) up to the point in time $t_1$. If use is made of the possibility of further aniline being introduced into the reactor of step B.II) in step B.II.1), this is added to the aniline in step B.I.1) for the purposes of determining the instantaneous molar ratio, $A/F_{inst}$, during the period of time from $t_1$ to $t_2$. If such aniline added in step B.II.1) is mixed beforehand with acid so that it is present as anilinium salt, this changes nothing in the calculation since one mole of aniline reacts with one mole of acid to form one mole of anilinium salt. For the purposes of calculating the instantaneous molar ratio $A/F_{inst}$, this can thus be carried out as if all aniline (1) were present in free form.

The ratio of aniline (1) to formaldehyde (2) prevailing instantaneously during start-up, $A/F_{inst}$, is, according to the invention, always set so that the target value $A/F_{target}$ is fundamentally approached from above and not from below. This means that, for example, in the case of a desired $A/F_{target}$ ratio of 2.0, an instantaneous molar ratio of aniline (1) to formaldehyde (2), $A/F_{inst}$, of at least 2.1 is actually maintained during the period of time from $t_1$ to $t_2$. After the desired load has been attained, i.e. after the desired formaldehyde mass flow rate $m_{2,intended}$ has been reached at the point in time $t_2$, the molar ratio of aniline (1) to formaldehyde (2) is then set to $A/F_{target}$, in the chosen example thus to 2.0. Theoretically, two mole of aniline react with one mole of formaldehyde to form one mole of diaminodiphenylmethane, so that this example describes the case of the stoichiometric mode of operation.

In the real system, higher homologs are always also formed in addition to the isomeric diaminodiphenylmethanes at an $A/F_{target}$ ratio of 2.0 in the target formulation, so that part of the aniline introduced is present unchanged in the resulting reaction mixture at the end of the reaction.

Embodiments of the process of the invention are described below. They can be combined with one another in any way, unless the contrary is clear from the context.

If a production plant for preparing MDA is to be operated at an intended load $m_{2,intended}$ of x [kg(formaldehyde)/h], this intended load can be achieved by firstly setting the load $m_{2,intended}$ to a value of, for example, 0.25 x and then increasing the load via the intermediate stages $m_2$=0.50 x and $m_2$=0.75 x over a period of time t to the value 1112=x=$m_{2,intended}$.

The start-up of MDA production occurs without problems first and foremost when the load increase from an initial value $m_2$=0.0 x to $m_2$=x can be carried out swiftly and continuously and preferably linearly (with steps or steplessly) taking into account all operationally relevant parameters. To counter poor mixing of amine with formaldehyde in the reaction space and also not to lose productivity, the load should be increased promptly and steplessly to at least 30% of the target load (i.e. generally the nominal load; however, the target load can also deviate from the nominal load, e.g. in the case of low demand) of the reaction line. Should, for example for technical reasons or because of low demand for product, the desired target load be lower than the nominal load, i.e. half-load operation, the procedure is analogous.

The load is preferably increased promptly to from 30% to 95%, very preferably to from 35% to 80% and very particularly preferably to from 40% to 60%. The start-up procedure until attainment of at least 30% of the nominal load should be carried out within a start-up time of less than 30 hours, preferably less than 20 hours, particularly preferably less than 10 hours and very particularly preferably less than 5 hours.

This example is naturally only illustrative for many possible start-up procedures, the precise configuration of which depends on the specific circumstances of a production plant and therefore cannot be generalized. However, a feature which all conceivable start-up procedures have in common is that the desired intended load of x is reached only after a period of time has elapsed. This period of time is referred to as the start-up time. The term start-up refers in particular to the restarting of the plant after a short stoppage or a planned stoppage.

If two or more MDA reactor lines are to be operated in parallel, it is then possible for one reactor line to be started and the other reactor lines to be started up in succession, but this does not have to be the case. When the auxiliary systems are dimensioned so that, for example, they can take up and process further the excess aniline, water of reaction and the water which is introduced into the process via aqueous aniline and formaldehyde without problems during start-up of the plant, it is then possible for all MDA reactor lines to be started up close to simultaneously.

In a further embodiment of the process of the invention, $t_1-t_0$ is >0.001 hour, preferably from >0.005 hour to 5 hours, particularly preferably from 0.01 hour to 3 hours, in both variants A) and B).

In a further embodiment of the process of the invention, $t_2-t_1$ is <30 hours in both variants A) and B). This period of time is preferably from >0 hour to <20 hours, particularly preferably <10 hours and very particularly preferably <5 hours.

In a further embodiment of the process of the invention, the mass flow rate $m_1$ in step I) is ≥1000 kg/hour in both variants A) and B). This mass flow rate is preferably from ≥2000 kg/hour to ≤200 000 kg/hour, more preferably from ≥3000 kg/hour to ≤100 000 kg/hour.

In a further embodiment of the process of the invention, the mass flow rate $m_{2,intended}$ in step I) is ≥300 kg/hour in both variants A) and B). This mass flow rate is preferably from ≥400 kg/hour to ≤100 000 kg/hour, more preferably from ≥500 kg/hour to ≤50 000 kg/hour.

The formaldehyde (2) used can, in both variants, originate from all known production processes for formaldehyde. Mention may be made merely by way of example of the silver catalyst process.

In a further embodiment of the process of the invention, the point in time $t_1$ is, in both variants A) and B), selected so that at this point in time the respective reactor (i.e. the reactor of step A.I) or of step B.II)) is filled with aniline (1) to from 1% to 99%, preferably from 10% to 90%, particularly preferably from 20% to 80%, of its capacity (based on the available interior volume of the reactor).

The process procedures of variants A) and B) in normal operation up to the point at which the crude product is obtained are described in more detail below:

The preparation of the crude diamines and polyamines of the diphenylmethane series according to variant A) can be summarized by way of example as follows:

a) key procedure of step A.I): aniline and formaldehyde are condensed in the absence of an acid catalyst in a reactor (the "aminal reactor") to form aminal and water and the resulting aminal is discharged from the aminal reactor, and b) water from step a), which originates mainly from water of condensation from the aminal reaction and water from the starting material formaldehyde, is at least partly separated off as aqueous phase from the reaction mixture from the aminal reaction, and c) key procedure of step A.II): the aminal from step b) is rearranged in the presence of an acid catalyst to form MDA.

The condensation of aniline and formaldehyde in step a) can be carried out by any method according to the prior art. Here, aniline and aqueous formaldehyde solution are normally condensed at molar ratios in the range from 1.5 to 20, preferably from 1.5 to 10 and particularly preferably from 1.5 to 6, at temperatures of from 20° C. to 120° C., preferably from 40° C. to 110° C. and particularly preferably from 60° C. to 100° C., to form aminal and water. The reactor of step A.I is operated at atmospheric pressure or under superatmospheric pressure. A pressure of from 1.05 to 5 bar absolute, very preferably from 1.1 to 3 bar and very particularly preferably from 1.2 bar to 2 bar absolute, preferably prevails. The pressure is maintained by means of pressure regulating valves or by connecting the offgas systems of the aminal reactor and the overflow of the aminal separator. The aminal separator and the outflow of the aqueous phase are preferably heated in order to prevent caking. Suitable aniline grades are, for example, described in EP 1 257 522 B1, EP 2 103 595 A1 and EP 1 813 598 B1. Preference is given to using technical grades of formalin (aqueous solution of formaldehyde) containing from 30% by mass to 50% by mass of formaldehyde in water. However, formaldehyde solutions having lower or higher concentrations or else the use of gaseous formaldehyde are also conceivable.

The reactor of step A.I) (also referred to as "aminal reactor") and the reactor of step A.II) (also referred to as "rearrangement reactor") are advantageously different from one another. However, carrying out steps A.I) and A.II) in the same reactor is not ruled out.

Firstly, "feed aniline" can be placed in the aminal reactor at temperatures of from 10° C. to 60° C. A certain amount of aniline is also placed in the aminal separator in order to provide protection for the aminal pump which pumps the aminal to the rearrangement reactor. The feed aniline is made up of fresh aniline and optionally aniline from the MDA distillation (described further below; see step h)) and optionally aniline from the wastewater treatment.

Then, for example while aniline has already been introduced, the formalin is added to the well stirred, initially charged aniline, and the total plant from feed streams to product offtake should be ready for operation. The aminal reactor is equipped with a heat exchanger in order to remove the heat of reaction involved. As an alternative, the feed aniline can also be appropriately cooled. Theoretically, cooled formalin could also be used for taking up the heat of reaction. At the beginning of the introduction of formalin into the reaction space, an "infinite" excess of aniline is present.

At low A/F$_{target}$ ratios, there is a risk of deposition of solids ("aminal solids") in the aminal separator. A "formalin split" in which only part of the formalin required for attaining the A/F$_{target}$ value is introduced into the aminal reaction and the remaining formalin is fed into the reaction mixture immediately before, at the same time as or after the introduction of acid makes it possible to work with a sufficiently high molar ratio of aniline to formaldehyde in the aminal section in order to prevent solids formation. In addition, it is possible to work in a range in which phase separation proceeds quickly (the duration of phase separation goes through a minimum as a function of the molar ratio of aniline to formaldehyde).

Until the point in time $t_2$ is reached, aniline is introduced in such amounts that at least 1.05 times the $A/F_{target}$ ratio provided in the target formulation is maintained. Subsequently, the mass flow rate $m_1$ of aniline is modified so that the $A/F_{target}$ ratio provided in the target formulation is adhered to.

The starting materials aniline and formalin are preferably introduced after mixing from above as reaction mixture into the aminal reactor. The reaction mixture which is formed in the aminal reactor and contains the aminal is conveyed via a siphon into the aminal separator. The level in the aminal reactor is maintained by means of the siphon and contact of aminal reaction solution with the starting materials in the mixing apparatus, which would result in a blockage, is prevented. It is likewise conceivable, although not preferred, to supply the starting materials to the aminal reactor from below and operate the reactor with overflow.

In step b), the organic aminal phase and the aqueous phase are separated at temperatures of from 20° C. to 120° C., preferably from 40° C. to 110° C., particularly preferably from 60° C. to 100° C., preferably at ambient pressure. The phase separation can also be carried out under slightly superatmospheric pressure.

The rearrangement of the aminal in step c) occurs in the presence of an acid catalyst, usually a strong mineral acid such as hydrochloric acid. Preference is given to using mineral acid in a molar ratio of mineral acid to aniline of from 0.001 to 0.9, preferably from 0.05 to 0.5. It is naturally also possible to use solid, acid catalysts as described in the literature. Here, formaldehyde can be introduced into a mixture of aniline and acid catalyst and the reaction solution can be reacted to completion by stepwise heating. As an alternative, aniline and formaldehyde can also firstly be prereacted and subsequently admixed, with or without prior removal of water, with the acid catalyst or a mixture of further aniline and acid catalyst, after which the reaction solution is reacted to completion by stepwise heating. This reaction can be carried out continuously or batchwise by one of the numerous methods described in the literature (e.g. in EP 1 616 890 A1 or EP 127 0544 A1). Suitable hydrochloric acid grades are, for example, described in EP 1 652 835 A1.

The preparation of the crude diamines and/or polyamines of the diphenylmethane series according to variant B) can be summarized by way of example as follows:
a) key procedure of step B.I): aniline and acid are reacted in the absence of formaldehyde to give a reaction mixture containing the anilinium salt of the acid used, and
b) key procedure of step B.II): the reaction mixture from step a), which contains the anilinium salt of the acid used, is admixed with formaldehyde and rearranged to form MDA.

The reaction of aniline and acid, preferably hydrochloric acid, in step a) can be carried out by a method according to the prior art. The further description is given for the example of aqueous hydrochloric acid, but other acids can also be used. Aniline and an aqueous hydrochloric acid are normally reacted at molar ratios of aniline to acid in the range from 1.6 to 100, preferably from 3.3 to 20. This reaction can be carried out in an upstream reactor or a mixing section, with the reaction mixture optionally being able to be temporarily stored in a reservoir. This reaction can optionally be carried out in the same reactor in which the subsequent reaction of the reaction mixture of aniline and acid with formaldehyde takes place. Suitable aniline grades are, for example, described in EP 1 257 522 B1, EP 2 103 595 A1 and EP 1 813 598 B1. Suitable hydrochloric acid grades are, for example, described in EP 1 652 835 A1.

"Feed aniline" can firstly be placed in the reactor at temperatures of from 10° C. to 60° C. The feed aniline is made up of fresh aniline and optionally aniline from the MDA distillation (described in more detail further below; see step h)) and optionally aniline from the wastewater treatment.

Then, for example while aniline is already being introduced, the hydrochloric acid is added to the initially charged aniline, with care being taken to ensure good mixing. This good mixing can be achieved by stirring by means of a stirrer or else by circulation (by means of pumps) of the reaction mixture or by a combination of stirring and circulation. The total plant from feed streams to product offtake should optionally be ready for operation. The reaction apparatus can, if necessary, be equipped with an internal or external heat exchanger in order to be able to remove the heat of reaction evolved. As an alternative, the feed aniline and/or the hydrochloric acid can be appropriately cooled. A further alternative is the use of evaporative cooling to remove the heat of reaction.

In step b), the aniline hydrochloride-containing reaction mixture from step a) is reacted with aqueous formaldehyde solution. Here, formaldehyde can be introduced into a mixture of aniline and acid catalyst and the reaction solution can be reacted to completion by stepwise heating, as described, for example, in EP 1 053 222 A1. The reaction is usually carried out at temperatures of from 20° C. to 150° C.

The reactor of step B.I) and the reactor of step B.II) are advantageously different from one another. However, carrying out steps B.I) and B.II) in the same reactor is not ruled out. This reaction can be carried out continuously, semicontinuously or batchwise.

Preference is given to using technical grades of formalin (aqueous solution of formaldehyde) containing from 30% by mass to 50% by mass of formaldehyde in water. However, formaldehyde solutions having lower or higher concentrations or else the use of gaseous formaldehyde are also conceivable.

In the case of a semicontinuous or batchwise reaction, an "infinite" excess of aniline in the form of free aniline and aniline hydrochloride is present at the commencement of the introduction of formaldehyde into the reaction apparatus. Up to attainment of the point in time $t_2$, formaldehyde is introduced in such amounts that at least 1.05 times the $A/F_{target}$ ratio provided in the target formulation is maintained. After the start-up procedure, the amounts of aniline and/or formaldehyde are modified so that the $A/F_{target}$ ratio provided in the target formulation is adhered to.

In both variants A) and B), a crude reaction mixture containing diamines and polyamines of the diphenylmethane series is obtained (in variant A) in step c) and in variant B) in step b)). The work-up of this reaction mixture is, regardless of whether variant A) or B) is used, preferably carried out as follows:
d) the reaction mixture containing diamines and polyamines of the diphenylmethane series from step A.c) or B.b) is neutralized, and
e) the neutralized reaction mixture containing diamines and polyamines of the diphenylmethane series is separated in a separation vessel into an organic phase containing diamines and polyamines of the diphenylmethane series and an aqueous phase, and f) the organic phase containing diamines and polyamines of the diphenylmethane series is purified further by means of washing liquid in a washing vessel, and g) the mixture obtained in this way is separated in a separation vessel into an organic phase containing diamines and polyamines of the diphenylmethane series and an aqueous phase, and h) the washed organic phase containing diamines and polyamines of the diphenylmethane series is freed of water and aniline by distillation.

In step d), the reaction mixture containing the diamines and polyamines of the diphenylmethane series is neutralized, optionally with addition of water and/or aniline. According to the prior art, the neutralization is usually carried out at temperatures of, for example, from 90° C. to 100° C. without addition of further substances. However, it can also be carried out at a different temperature level, for example in order to accelerate the degradation of interfering by-products. Suitable bases are, for example, the hydroxides of the alkali and alkaline earth elements. Aqueous NaOH is preferably employed. The base used for neutralization is preferably used in amounts of greater than 100%, particularly preferably from 105% to 120%, of the amount which is stoichiometrically required to neutralize the acid catalyst used (see EP 1 652 835 A1).

Subsequently, in step e), the neutralized reaction mixture containing the diamines and polyamines of the diphenylmethane series is separated into an organic phase containing diamines and polyamines of the diphenylmethane series and an aqueous phase. This can be assisted by addition of aniline and/or water. If the phase separation is assisted by addition of aniline and/or water, these are preferably added with intensive mixing as early as the neutralization. Mixing here can be effected in mixing sections having static mixers, in stirred vessels or cascades of stirred vessels or else in a combination of mixing sections and stirred vessels. The neutralized reaction mixture which has been diluted by addition of aniline and/or water is subsequently preferably fed into an apparatus which, owing to its configuration and/or internals, is particularly suitable for separation into an organic phase containing MDA and an aqueous phase, preferably phase separation or extraction apparatuses corresponding to the prior art, as are described, for example, in Mass-Transfer Operations, 3rd Edition, 1980, McGraw-Hill Book Co, pp. 477 to 541, or Ullmann's Encyclopedia of Industrial Chemistry (Vol. 21, Liquid-Liquid Extraction, E. Müller et al., pages 272-274, 2012 Wiley-VCH Verlag GmbH & Co. KGaA, Weinheim, DOI: 10.1002/14356007.b03_06.pub2) or in Kirk-Othmer Encyclopedia of Chemical Technology (see "http://onlinelibrary.wiley.com/book/10.1002/0471238961", published online: Jun. 15, 2007, pages 22-23) (mixer-settler cascade or settling vessel).

In step f), washing of the organic phase with water follows, and in step g) the aqueous phase is separated off again in order to remove residual contents of salt (preferably as described in DE-A-2549890, page 3).

In step h), water and aniline are separated off by distillation from the organic phase containing diamines and polyamines of the diphenylmethane series obtained in step g), as described in EP 1 813 597 B1. The organic phase obtained in step g) preferably has a composition, based on the weight of the mixture, of 5-15 percent by weight of water and, depending on the ratios of aniline and formaldehyde used, 5-90 percent by weight, preferably 5-40 percent by weight, of aniline and 5-90 percent by weight, preferably 50-90 percent by weight, of diamines and polyamines of the diphenylmethane series. After exit from the phase separation in step g), the organic phase containing diamines and polyamines of the diphenylmethane series usually has a temperature of 80° C.-150° C.

The diamines and polyamines of the diphenylmethane series which have been obtained in this way can be reacted with phosgene in an organic solvent by the known methods under inert conditions to form the corresponding diisocyanates and polyisocyanates of the diphenylmethane series, viz. MDI. Here, the phosgenation can be carried out by one of the processes known from the prior art (e.g. DE-A-844896 or DE-A-19817691).

If the conditions according to the invention are adhered to during the start-up of step I), the following advantages are obtained for both variants A) and B):

i) avoidance of blockages and deposits in reactors, in cooling devices, separators and cooling circulation pumps and thus avoidance of a second start-up procedure because the plant does not have to be run down again and opened for the purpose of cleaning the equipment.

ii) saving of energy because the start-up procedure does not have to be carried out a second time due to formation of blockages and deposits and the resulting shutdown of the plant for the purpose of cleaning the equipment.

iii) an increase in the productivity of the plant because the reactor running times are increased because the cleaning times for removing blockages and deposits are dispensed with.

iv) avoidance or reduction of precipitates, caking and blockages on the equipment (reactors, cooling devices, separators and cooling circulation pumps) and, associated therewith, a lengthening of the operating time of the process.

v) reduced waste after cleaning of the equipment (high molecular weight solids) and saving of incineration costs.

vi) avoidance of out-of-specification product which can be formed by multiple poor starting up and running down: such poor quality running-down product thus does not have to be blended with good-quality MDA or in the worst case be incinerated.

vii) improved phase separation between aqueous phase and organic phase due to the absence of high molecular weight compounds which have an adverse effect on the phase separation.

The present invention is illustrated with the aid of the following drawings and examples, but without being restricted thereto.

Figure 2:
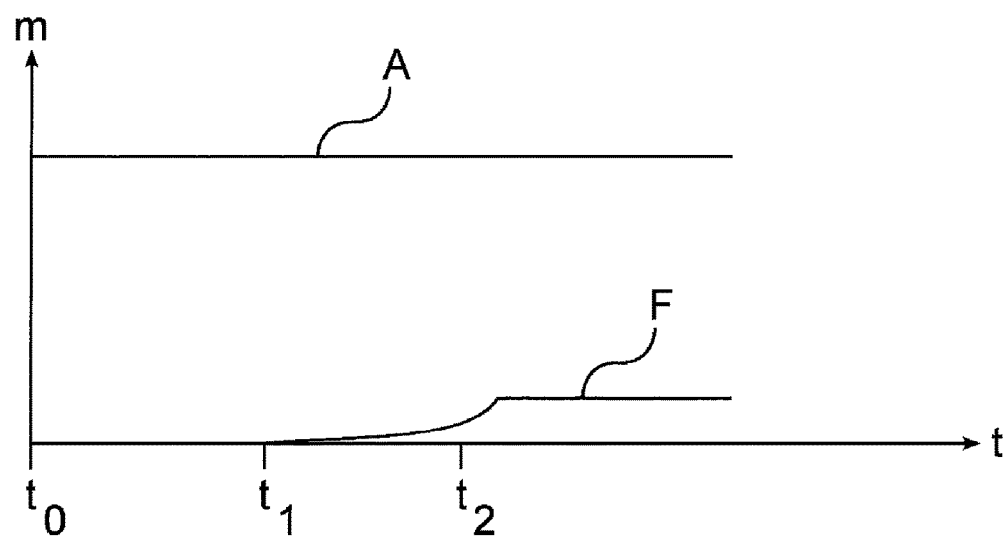

The drawings show:

FIG. 1-2 the course over time of the mass flow rates of aniline and formaldehyde in the process of the invention.

FIG. 1 shows the course over time of the mass flow rates of aniline and formaldehyde in an embodiment of variant A) of the process of the invention, the time t is plotted on the x axis and mass flow rates m are plotted on the y axis. At the point in time to, the mass flow rate of aniline ($m_1$, in the figure denoted by "A") is already constant in the aminal reactor, designated in the terminology of the present invention as reactor of step A.I). and that of formaldehyde ($m_2$, in the figure denoted by "F") is zero.

It is now decided that production is to be started. For this purpose, the mass flow rate of formaldehyde into the first reactor is increased at the point in time $t_1$ while leaving the magnitude of the mass flow rate of aniline unchanged until the mass flow rate of formaldehyde has risen to the target value $m_{2,intended}$ at the point in time $t_2$.

It can be seen that the mass flow rate of aniline introduced into the aminal reactor is greater than the mass flow rate of formaldehyde to such an extent that the molar ratio of aniline to formaldehyde is at least 2 at any point of time during start-up of the reaction.

During the time between $t_1$ and $t_2$, the formaldehyde already present in the first reactor can react to completion with the aniline. Finally, there is no free formaldehyde present in the aminal reactor.

FIG. 2 shows, in a manner analogous to FIG. 1, the course over time of the mass flow rates of aniline and formaldehyde in a further embodiment of the variant A) of the process of the invention. Here, the introduction of formaldehyde from the point in time $t_1$ is not linear but follows a curve.

EXAMPLES

General Conditions for the Preparation of MDA in a Run-in Production Plant (Before Commencement of the Running-Down Procedure)

In a continuous reaction process (step a)), 24.3 t/h of feed aniline (containing 90% by mass of aniline) and 9.9 t/h of 32% strength aqueous formaldehyde solution (molar ratio of aniline to formalin 2.1:1) were mixed and reacted at 90° C. and 1.4 bar absolute in a stirred reaction vessel to form aminal. The reaction vessel was provided with a cooler having a cooling circulation pump. The reaction mixture leaving the reaction vessel was conveyed into a phase separation apparatus (aminal separator) (step b)).

After phase separation to remove the aqueous phase, the organic phase was admixed in a mixing nozzle with 30% strength aqueous hydrochloric acid (degree of protonation 10%, i.e. 0.1 mol of HCl are added per mole of amino groups) and fed into the first rearrangement reactor. The rearrangement reaction was carried out at from 45° C. to 165° C. in a reactor cascade (step c)).

After the reaction was complete, the reaction mixture obtained was admixed with 32% strength sodium hydroxide solution in a molar ratio of sodium hydroxide to HCl of 1.1:1 and reacted in a stirred neutralization vessel (step d)). The temperature was 115° C. The absolute pressure was 1.4 bar. The neutralized reaction mixture was subsequently separated in a neutralization separator into a lower, aqueous phase, which is conveyed to a wastewater collection vessel, and an organic phase (step e)).

The upper, organic phase was conveyed to washing and washed with condensate and/or water from the side stream from the wastewater column (aniline/water mixture) in a stirred washing vessel (step f)). After the washing water had been separated off in a washing water separator (step g)), the crude MDA obtained in this way was freed of water and aniline by distillation, with 17 t/h of MDA being obtained as bottom product (step h)).

Example 1 (Comparative Example): Start-Up of the MDA Plant, with Formalin being Initially Charged After maintenance work in the MDA plant, the empty, stirred aminal reactor was filled with 32% strength aqueous formaldehyde solution until the formaldehyde ran over via the siphon into the aminal separator. When the aminal reactor had been filled to this extent, the formalin flowed at a rate of 4.95 t/h into the stirred aminal reaction vessel, which corresponded to 50% of the nominal load.

The aniline conduit was then opened. The reaction commenced immediately and the reaction mixture was regulated to 90° C. by means of a cooling water circuit. The amount of aniline which is to be introduced into the aminal reactor during a planned start-up time of 45 minutes should be increased steplessly from 0 t/h to 12.2 t/h of feed aniline. After 2 minutes, the plant had to be shut down because the aminal vessel, the aminal cooler and the aminal separator were blocked and the aminal cooling circulation pump was likewise blocked with solid and did not run.

Example 2 (Comparative Example): Start-Up of the MDA Plant, with Introduction of Formalin and Aniline being Commenced at the Same Time After repair work in the MDA plant, the aminal reaction was started up by a 32% strength aqueous formaldehyde solution and feed aniline (containing 90% by mass of aniline) being introduced at the same time into the empty aminal reactor. The amount of the two starting materials introduced into the stirred aminal reactor during the start-up time t of 45 minutes was increased steplessly from 0 t/h to 4.95 t/h of 32% strength formaldehyde solution and from 0 t/h to 12.2 t/h of feed aniline (containing 90% by mass of aniline).

After 2 days of production, the aminal reactor had to be taken out of operation because an extremely viscous, honey-like solid (insoluble polymeric amines) had precipitated in the aminal separator and the outlet of the aminal separator had become blocked, which required cleaning.

Example 3 (According to the Invention): Start-Up of the MDA Plant, with Aniline being Initially Charged After maintenance work in the aminal part of the MDA plant, the aminal reactor was filled with feed aniline (containing 90% by mass of aniline) until aniline flowed over via the siphon into the aminal separator. When the aminal reactor had been filled to this extent, the feed aniline flowed at a rate of 12.2 t/h into the stirred aminal reaction vessel. The formalin conduit was then opened. The reaction commenced immediately and the reaction mixture was regulated to 90° C. by means of a cooling water circuit. The pressure in the aminal reactor was 1.4 bar absolute during the start-up phase.

During a start-up time of 45 minutes, the amount of 32% strength aqueous formaldehyde solution introduced into the aminal reactor was increased steplessly from 0 t/h to 4.95 t/h, which corresponded to 50% of the nominal load and an A/F ratio of 2.1:1. The reaction mixture was subsequently conveyed from the aminal reactor into a phase separation apparatus in which the water of reaction from the aminal reaction was separated off. The remaining organic phase was then pumped into the first rearrangement tank, with a 30% strength aqueous hydrochloric acid corresponding to a degree of protonation of 10% (i.e. 0.1 mol of HCl are added per mole of amino groups) being introduced at the same time via a mixing nozzle into the inlet for the organic phase (aminal) into the first rearrangement tank. The rearrangement reaction took place at from 50° C. to 150° C. in a reactor cascade (step c)). After the reaction was complete, the reaction mixture obtained was worked up as described in the general conditions for the preparation of MDA.

In the mode of operation according to the invention, a blockage in the aminal vessel, in the aminal cooler, in the aminal separator and stoppage of the aminal cooling circulation pump due to deposits of solid were avoided during the start-up phase. The aminal vessel could be operated over a long production cycle of a number of months. The formation of undesirable by-products such as insoluble polymeric amines, etc., was significantly reduced and latter blending of the start-up product with pure MDA or in the worst case incineration of the start-up product could be dispensed with.

Example 4 (According to the Invention): Start-Up of the MDA Plant, with Aniline being Initially Charged in the Condensation and Aniline Hydrochloride being Initially Charged in the Rearrangement After a shutdown of the MDA plant, the empty aminal reactor was filled with feed aniline (containing 90% by mass of aniline) until aniline flowed over via the siphon into the aminal separator. When the aminal reactor had been filled to this extent, the feed aniline flowed at a rate of 12.2 t/h into the stirred aminal reaction vessel. The formalin conduit was then opened.

The reaction commenced immediately and the reaction mixture was regulated to 90° C. The pressure in the aminal reactor was 1.4 bar absolute during the start-up phase. During a start-up time of 45 minutes, the amount of 32% strength formaldehyde solution which was introduced into the aminal reactor was increased steplessly from 0 t/h to 4.95 t/h, which corresponded to 50% of the nominal load.

The reaction mixture was subsequently conveyed from the aminal reactor into a phase separation apparatus in which the water of reaction from the aminal reaction was separated off. The remaining organic phase was then pumped into the first rearrangement reactor which had been filled to a level of 60% with aniline hydrochloride. A 30% strength aqueous hydrochloric acid corresponding to a degree of protonation of 10% (i.e. 0.1 mol of HCl are added per mole of amino groups) was at the same time introduced via a mixing nozzle into the inlet for aminal into the first rearrangement tank. The rearrangement reaction was carried out at from 50° C. to 165° C. in a reactor cascade (step c)). After the reaction was complete, the reaction mixture obtained was worked up as described in the general conditions for the preparation of MDA.

In the mode of operation according to the invention, a blockage in the aminal vessel, in the aminal cooler, in the aminal separator and also stoppage of the aminal cooling circulation pump by deposits of solid were avoided. The aminal vessel could be operated over a long production cycle of a number of months. In addition, no problems with deposits occurred in the first rearrangement reactor. The formation of undesirable by-products such as insoluble polymeric amines, etc., was significantly reduced, and later blending of the start-up product with pure MDA or in the worst case incineration of the start-up product could be dispensed with.

The invention claimed is:

1. A process for preparing diamines and polyamines of the diphenylmethane series (MDA) by reaction of aniline (1) and formaldehyde (2) at a desired molar ratio of aniline (1) to formaldehyde (2) of $A/F_{target}$, which comprises the steps: either according to a variant A)
   A.I) reacting aniline (1) and formaldehyde (2) in the absence of an acid catalyst (3) in a reactor to form an aminal, with aniline (1) and formaldehyde (2) being introduced into the reactor, and subsequent separation of the reaction mixture obtained into an aqueous phase and an organic, aminal-containing phase; and
   A.II) reacting at least part of the organic, aminal-containing phase obtained in step A.I) with acid (3) in a reactor, with the aminal reacting to form diamines and polyamines of the diphenylmethane series;

wherein the following steps are carried out for start-up of the process and/or resumption of the process after an interruption of at least the step A.I):
   A.I.1) introducing aniline (1) into the reactor of step A.I) at a mass flow rate $m_1$ commencing at the point in time $t_0$;
   A.I.2) introducing of formaldehyde (2) into the reactor of step A.I), commencing at a point in time $t_1$, starting from a mass flow rate $m_2=0$ at the point in time $t_1$ to a mass flow rate $m_2=m_{2,intended}$ at the point in time $t_2$, where $t_2>t_1>t_0$; and
   A.II.1) in the case of interruption of the step A.II) too, introducing acid (3) into the reactor of step A.II) at the latest when, as soon as or after, organic, aminal-containing phase is introduced for the first time into the reactor of step A.II);
   where the introduction of aniline (1) in step A.I.1) and the introduction of formaldehyde (2) in step A.I.2) occur in such a way that the instantaneous molar ratio of
   the total aniline (1) introduced into the reactor of step A.I)
   to
   the total formaldehyde (2) introduced into the reactor of step A.I),
   $A/F_{inst}$, is always $\geq 2$ and $\geq 1.05 \cdot A/F_{target}$, during the period of time from $t_1$ to $t_2$;
or according to a variant B),
   B.I) reacting aniline (1) and acid (3) in a reactor to form a reaction mixture containing the anilinium salt of the acid (3) used; and
   B.II) reacting of at least part of the reaction mixture obtained in step B.I) with formaldehyde (2) in a reactor, forming diamines and polyamines of the diphenylmethane series;
wherein the following steps are carried out for the start-up of the process and/or the resumption of the process after an interruption of the steps B.I) and B.II);
   B.I.1) introducing aniline (1) into the reactor of step B.I) at an aniline mass flow rate $m_1$ commencing at the point in time $t_0$;
   B.I.2) introducing of acid (3) before, simultaneously with or after introduction of aniline (1);
   B.II.1) introducing of formaldehyde (2) into the reactor of step B.II), optionally together with further aniline (1), optionally together with further acid (3), commencing at a point in time $t_1$, proceeding from a mass flow rate $m_2=0$ at the point in time $t_1$ to a mass flow rate $m_2=m_{2,intended}$ at the point in time $t_2$, where $t_2>t_1>t_0$;
   where the introduction of aniline (1) in step B.I.1) and optionally in step B.II.1) and the introduction of formaldehyde (2) in step B.II.1) occur in such a way that the instantaneous molar ratio of
   the total aniline (1) introduced into the reactor of step B.I) and, if present, the total aniline (1) introduced into the reactor of step B.II)
   to
   the total formaldehyde (2) introduced into the reactor of step B.II),
   $A/F_{inst}$, is always $\geq 2$ and $\geq 1.05 \cdot A/F_{target}$ during the period of time from $t_1$ to $t_2$.

2. The process as claimed in claim 1, wherein the steps I) and II) of both variants are carried out in a continuous process.

3. The process as claimed in claim 1, wherein $A/F_{target}$ has a value of from 1.5 to 20 in both variants.

4. The process of claim 3, wherein $A/F_{target}$ has a value of from 1.5 to 10 in both variants.

5. The process of claim 4, wherein $A/F_{target}$ has a value of from 1.5 to 6 in both variants.

6. The process as claimed in claim 1, wherein $t_1-t_0$ is >0.001 hour in both variants.

7. The process as claimed in claim 1 wherein $t_2-t_1$ is <30 hours in both variants.

8. The process as claimed in claim 1, wherein the mass flow rate $m_1$ is ≥1000 kg/hour in both variants.

9. The process as claimed in claim 1, wherein the mass flow rate $m_{2,intended}$ is ≥300 kg/hour in both variants.

10. The process as claimed in claim 1, wherein, in both variants, the point in time $t_1$ is selected so that at this point in time the respective reactor is full of aniline to an extent of from 1% to 99% of its maximum capacity.

11. The process of claim 10, wherein, in both variants, the point in time $t_1$ is selected so that at this point in time the respective reactor is full of aniline to an extent of from 10% to 90% of its maximum capacity.

12. The process of claim 11, wherein, in both variants, the point in time $t_1$ is selected so that at this point in time the respective reactor is full of aniline to an extent of from 20% to 80% of its maximum capacity.

* * * * *